United States Patent [19]
Marquez et al.

[11] Patent Number: 6,022,830
[45] Date of Patent: Feb. 8, 2000

[54] CROP HARVESTING METHOD USING A BENZYLOXPHENYL URACIL

[75] Inventors: Mario S. Marquez, Hahira, Ga.; Frederick W. Hotzman, Morrisville, Pa.; James T. Bahr, Hopewell, N.J.

[73] Assignee: FMC Corporation

[21] Appl. No.: 08/892,617

[22] Filed: Jul. 14, 1997

[51] Int. Cl.[7] .................................................. A01N 43/48
[52] U.S. Cl. ............................................................ 504/168
[58] Field of Search ............................................... 504/168

[56] References Cited

U.S. PATENT DOCUMENTS 5,344,812  9/1994  Theodoridis ............................ 504/234

OTHER PUBLICATIONS

Edmisten, Keith, "*Cotton Defoliation*", North Carolina Cooperative Extension, Jan. 1995.

*Primary Examiner*—Allen J. Robinson
*Attorney, Agent, or Firm*—FMC Corporation

[57] ABSTRACT

Described herein is a method for defoliating a crop plant or desiccating a crop vine plant to aid in harvesting the crop which comprises the step of applying to the plant an effective amount of a composition comprising a benzyloxyphenyluracil having the formula

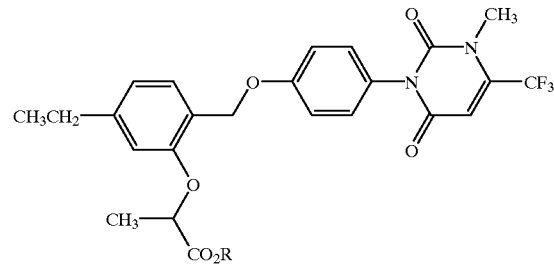

where R is an alkyl group of one to six carbons, in admixture with an agriculturally suitable carrier. The method is particularly effective at low use rates as an aid for harvesting potatoes and cotton.

7 Claims, No Drawings

CROP HARVESTING METHOD USING A BENZYLOXPHENYL URACIL

BACKGROUND OF THE INVENTION

This invention pertains generally to a method that aids in harvesting crops by application to the crop of a certain compound prior to harvest, so as to cause crop defoliation or vine dessication. More specifically it pertains to a method that aids in harvesting crops, particularly cotton or potatoes, by application of an alkyl 2-(5-ethyl-2-(4-(1-methyl-6-trifluoromethyl-2,4-(1H, 3H)-pyrimidinedion-3-yl) phenoxymethyl)phenoxy)propionate.

It is well known that the harvesting of certain crops may be aided by the use of substances that cause crop defoliation or vine dessication. For example, cotton defoliation prior to harvest has several potential benefits. The removal of leaves (1) eliminates the main source of stain and trash, resulting in better grade cotton, (2) allows the cotton picker to operate faster and more efficiently, (3) allows quicker drying of dew so that picking can start earlier in the day, (4) helps straighten lodged plants for more efficient picking, (5) retards boll rot, and (6) helps stimulate boll opening. How well the cotton defoliates will often effect the yield and fiber quality of the cotton. (K. Edmisten, Center for Integrated Pest Management, North Carolina State University, via internet publication dated March, 1995).

For the harvesting of vine crops such as potatoes, vine desiccation is desired. Potatoes on dessicated vines are easier to harvest than those on living vines. In addition, potatoes on the killed vines are less likely to skin and bruise during harvesting. Where skinning occurs, the skinned areas of a potato are susceptible to discoloration and soft rot infection. Furthermore, skinned potatoes lose weight more rapidly and appear untidy.

Examples of compounds that are commonly used as cotton defoliants include S,S,S-tributyl phosphorotrithioate, also known as butifos or Def®, and 1-phenyl-3-(1,2,3-thiadiazol-5-yl)urea, also known as thidiazuron or Dropp®. Compounds that are commonly used for potato vine desiccation are 1,1'-ethylene-2,2'-bipyridyldiylium ion as the dibromide monohydrate salt, also known as diquat, (+/-)-2-amino4-(hydroxymethylphosphinyl)butanoic acid, also known as glufosinate, and 1,1'-dimethyl-2,2'-bipyridyldiylium ion as the dichloride salt, also known as paraquat. Among the limitations of some of these commonly used harvest aids is the need for high use rates. Thus, there is a continuing demand for new substances that promote crop defoliation or vine desiccation at low use rates and in a safe manner.

U.S. Pat. No. 5,344,812 (Theodoridis) describes herbicidal compounds having the formula

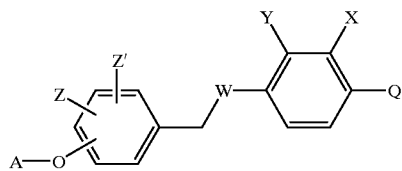

in which A is a derivative of an alkanoate bonded to the phenoxy oxygen at the alpha carbon; Q is one of several heterocyclic rings; X is hydrogen, methyl, fluorine or chlorine; Y is hydrogen; W is oxygen or sulfur; Z is hydrogen, fluorine, chlorine, bromine, lower alkyl, or methoxy; and Z' is hydrogen, fluorine, or chlorine. When applied as postemergence herbicides these compounds were reported to exhibit very good control of a variety of weeds, but with no crop tolerance. Thus the compounds were considered excellent candidates as total vegetation control agents. The utility of these compounds as a harvest aid by causing crop defoliation or vine desiccation has not been reported.

SUMMARY OF THE INVENTION

It has now been discovered that certain alkyl 2-(5ethyl-2-(4-(1-methyl-6-trifluoromethyl-2,4-(1H, 3H)-pyrimidinedion-3-yl)phenoxymethyl)phenoxy)-propionates of formula I below are useful aids for the harvesting of crops. In a preferred embodiment of the invention the compound is applied to cotton thereby causing cotton defoliation. In another preferred embodiment the compound is applied to potatoes thereby causing vine dessication. The method is effective using low rates of the compound.

DETAILED DESCRIPTION OF THE INVENTION

This invention pertains to a method for defoliating a crop plant or desiccating a crop vine plant to aid in harvesting the crop which comprises the steps of applying to the plant an effective amount of a composition comprising a benzyloxyphenyluracil having the formula I:

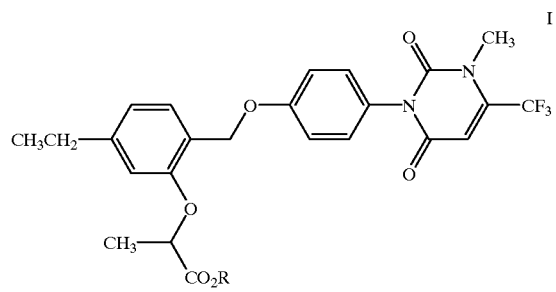

where R is an alkyl group of one to six carbons in admixture with an agriculturally suitable carrier. An effective amount of the composition is that amount sufficient to cause crop plant defoliation or vine desiccation as described below.

The benzyloxyphenyluracils of formula I are also known by the chemical name alkyl 2-(5-ethyl-2-(4-(1-methyl-6-trifluoromethyl-2,4-(1H, 3H)-pyrimidinedion-3-yl) phenoxymethyl)phenoxy)propionate. Representative benzyloxyphenyluracil compounds useful in the present invention are shown in Table 1.

TABLE 1

Representative Benzyloxyphenyluracils

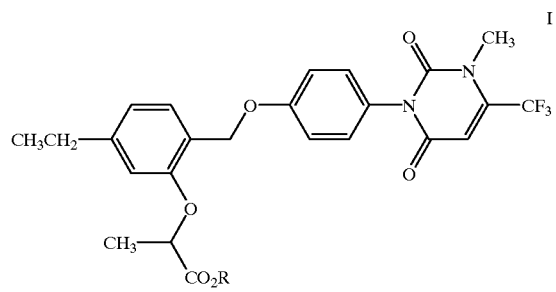

| Compound No. | R |
|---|---|
| Ia | $CH_3$ |
| Ib | $CH_2CH_3$ |
| Ic | $CH_2CH_2CH_3$ |
| Id | $CH(CH_3)_2$ |
| Ie | $(CH_2)_3CH_3$ |
| If | $CH_2CH(CH_3)_2$ |
| Ig | n-pentyl |
| Ih | n-hexyl |

The benzyloxyphenyluracils of formula I may be prepared by the methods taught in U.S. Pat. No. 5,344,812 or by methods analogous thereto. A preferred benzyloxyphenyluracil is a compound of formula I where R is methyl (Compound Ia).

One embodiment of the present invention relates to a method for defoliating a crop comprising the step of applying to the crop a crop defoliating amount of a composition comprising a benzyloxyphenyluracil of formula I in which R is an alkyl group of one to six carbons in admixture with an agriculturally acceptable carrier. In a preferred embodiment the crop is cotton.

Another embodiment of the present invention relates to a method for desiccating a crop comprising the step of applying to the crop a vine desiccating amount of a benzyloxyphenyluracil of formula I in which R is an alkyl group of one to six carbons in admixture with an agriculturally acceptable carrier. Examples of crops that may be desiccated by applying a benzyloxyphenyluracil according to this invention include potato, soybean and sunflower. In a preferred embodiment the crop is potato.

The compositions of the present method are prepared by combining effective amounts of the benzyloxyphenyluracils with adjuvants and carriers normally employed in the art for facilitating the dispersion of active ingredients for the particular utility desired, recognizing the fact that the formulation and mode of application of the harvest aid may affect its activity in a given application. Useful formulations include, but are not limited to, granules, emulsifiable concentrates, emulsifiable flowables, solutions, dispersions, wettable powders, suspensions, and suspension concentrates. A typical 240 g/l EC consists of the following:

| Component | Weight Percent |
|---|---|
| Compound (88.5%) | 25.99 |
| Emulsifier 1 | 4.80 |
| Emulsifier 2 | 3.20 |
| Naphthalene Organic Solvent | 66.01 | where the emulsifiers are blends of calcium sulfonate and nonionic surfactants such as those available from Stepan Company of Northfield, Ill. under the name Toximul® 709/710.

For an effective amount of the composition to cause crop plant defoliation, the amount of benzyloxyphenyluracil that may be used in the composition is in the range of about 15 to 150 grams of technical material per hectare. For an effective amount of the composition to cause vine desiccation, the amount of benzyloxyphenyluracil that may be used in the composition is in the range of about 15 to 75 grams per hectare. Adequate desiccation or defoliation may usually be achieved from a single application of the formulated benzyloxyphenyluracil.

The harvest aid is applied to the locus where the crops are to be harvested prior to the time of harvest. When the harvest aid is applied to achieve vine dessication, as for example in the harvesting of potatoes, the application should be made about seven to twenty-one days prior to harvest.

When the harvest aid is applied to achieve crop defoliation, as for example in the harvesting of cotton, the timing of defoliation is important. The proper timing of application of a defoliant is within the knowledge of one skilled in the art. For example, decisions for when to apply the harvest aid to cotton are typically based on such factors as the maturity of the cotton bolls and/or the percent of bolls that are open or unopen. Defoliation that occurs too early may result in lower yield. Defoliation that occurs too late may increase the chance of boll rot and may be less effective as a result of lower temperatures. Under normal conditions, it is generally safe to defoliate when about thirty to eighty-five percent of the bolls are open, preferably when about sixty percent of the bolls are open. The crop may then be harvested after about seven to twenty-one days after application of defoliant.

BIOLOGICAL RESULTS

The present method is very effective as a harvest aid with regard to both vine desiccation and crop defoliation. In particular, the method is very effective for potatoes and cotton. The efficacy of the benzyloxyuracils is shown below in the comparative testing of Compound Ia with commercial standards.

COTTON DEFOLIATION

Cotton defoliation activity was determined as follows. An appropriate amount of a 240 gram per liter emulsifiable concentrate formulation of Compound Ia was dissolved in sufficient water to provide rates of application of about 17, 35, 71, and 140 grams/hectare when sprayed using a small plot sprayer at a delivery rate in the range of 90–280 liters per hectare to the foliage of cotton in which 30–85% of the bolls were open. The solutions of Compound Ia sprayed onto the foliage contained 1% (v/v) of a crop oil concentrate consisting of a petroleum oil and surfactants/emulsifiers. There were four replicates for each rate of application wherein each replicate was sprayed onto two to four rows of cotton in a plot size of about 35 square meters or less. The test was conducted in a randomized complete block design. In each test of Compound Ia the standards butifos and thidiazuron were included either alone or in combination with each other. The rates of application for the standards varied from 840 to 1680 grams per hectare of butifos, and 56 to 224 grams per hectare of thidiazuron. Both of the standards, alone and in combination with each other, were also tested with and without the 1% (v/v) crop oil concentrate. The cotton test plots were assessed for percent defoliation at 14 days after treatment. Table 2 below shows the results of the defoliation tests.

TABLE 2

Cotton Defoliant Activity of Compound Ia and Commercial Standards

| Rates of Application (g/ha) | $COC^2$ 1% v/v[1] | Defoliation in 1995 Tests | Defoliation in 1996 Tests |
|---|---|---|---|
| 17 Compound Ia | + | 63 | 67 |
| 35 Compound Ia | + | 70 | 71 |
| 71 Compound Ia | + | 72 | 74 |
| 140 Compound Ia | + | 75 | 77 |

TABLE 2-continued

Cotton Defoliant Activity of Compound Ia and Commercial Standards

| Rates of Application (g/ha) | COC[2] 1% v/v[1] | Defoliation in 1995 Tests | Defoliation in 1996 Tests |
|---|---|---|---|
| 224 butifos | + | 65 | — |
| 1260 butifos | − | — | 69 |
| 1680 butifos | + | 81 | — |
| 112 thidiazuron | − | — | 61 |
| 840 butifos + 112 thidiazuron | + | 74 | — |
| 840 butifos + 56 thidiazuron | − | — | 77 |

[1]Treatments containing COC are indicated by a "+"
[2]COC is a generic crop oil concentrate consisting of 80–85% petroleum oil and 15–20% surfactants/emulsifiers.
The butifos used was manufactured by Chemagro Corp under the tradename Def ®. The thiadiazuron used was manufactured by Schering AG under the tradename Dropp ®. Testing was conducted in the United States.

The results show that Compound Ia is highly effective as a cotton defoliant when compared to the commercial standards butifos and thidiazuron which were applied at much higher rates.

POTATO DESICCATION

Potato desiccation activity was determined as follows. An appropriate amount of a 240 gram per liter emulsifiable concentrate formulation of Compound Ia was dissolved in sufficient water to provide rates of application of about 17–20, 35–40, and 60–70 grams per hectare when sprayed using a small plot sprayer at a delivery rate of 500 liters per hectare or less to the foliage of potatoes. The test materials were applied to the potatoes at the beginning of senescence. The solutions of Compound Ia sprayed onto the foliage contained 1% (v/v) of a crop oil concentrate consisting of a petroleum oil and surfactants/emulsifiers. There were two to four replicates for each rate of application wherein each replicate was sprayed onto rows of potatoes in a plot size of about 35 square meters or less. The test was conducted in a randomized complete block design. In each test of Compound Ia the standards diquat and glufosinate were included at rates of application of 1000 and 600 grams per hectare, respectively. The potato test plots were assessed for percent leaf and stem desiccation at about 11–15 and 19–22 days after treatment. Table 3 below shows the results of the desiccation tests.

TABLE 3

Potato Desiccation Activity of Compound Ia and a Commercial Standard

| Rates of Application (g/ha) | Percent Leaf Desiccation | | Percent Stem Desiccation | |
|---|---|---|---|---|
| | 11–15 DAT[2] | 19–22 DAT | 11–15 DAT | 19–22 DAT |
| Compound Ia | | | | |
| 17–20[1] | 88 | 91 | 78 | 89 |
| 35–40 | 90 | 92 | 81 | 91 |
| 60–70 | 92 | 95 | 85 | 95 |

TABLE 3-continued

Potato Desiccation Activity of Compound Ia and a Commercial Standard

| Rates of Application (g/ha) | Percent Leaf Desiccation | | Percent Stem Desiccation | |
|---|---|---|---|---|
| | 11–15 DAT[2] | 19–22 DAT | 11–15 DAT | 19–22 DAT |
| 1000 diquat | 95 | 97 | 85 | 95 |
| 600 glufosinate | 96 | 96 | 83 | 96 |

[1]All treatments with Compound A include COC (1% V/V).
[2]DAT is days after treatment.
Diquat used was manufactured by ICI. Glufosinate used was manufactured by Hoechst AG. These tests were conducted in the Europe in 1995 and 1996.

The results show that Compound Ia is highly effective as a potato vine dessicant when compared to the commercial standards diquat and glufosinate which were applied at much higher rates.

The active herbicidal compounds of the present invention may also be used in combination with other defoliants or dessicants. Such defoliants or dessicants include, for example, butifos, thidiazuron, paraquat, glufosinate, and diquat.

It is apparent that various modifications may be made in the formulations and application of the compounds of the present invention without departing from the inventive concepts herein, as defined in the claims.

We claim:

1. A method for defoliating a crop plant or desiccating a crop vine plant to aid in harvesting the crop which comprises the steps of applying to the plant an effective amount of a composition comprising a benzyloxyphenyluracil having the formula

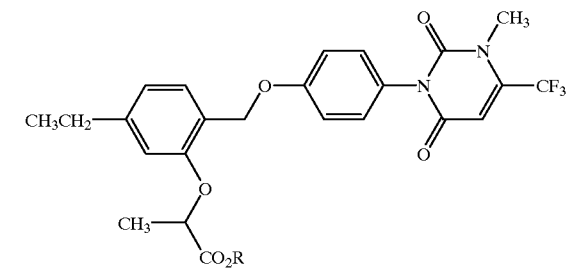

where R is an alkyl group of one to six carbons, in admixture with an agriculturally suitable carrier.

2. A method of claim 1 whereby the crop is defoliated by application of the composition.

3. A method of claim 2 where the crop is coffon.

4. A method of claim 1 whereby the vine of the crop is desiccated by application of the composition.

5. A method of claim 4 where the crop is potato.

6. The method of claim 1 further comprising the step of identifying said crop plant as being in need of defoliation.

7. The method of claim 1 further comprising the step of identifying said crop vine plant as being in need of desiccation.

* * * * *